United States Patent [19]
Filipowicz et al.

[11] Patent Number: 6,018,103
[45] Date of Patent: Jan. 25, 2000

[54] CHIMERIC PLANT GENES POSSESSING INDEPENDENT REGULATORY SEQUENCES

[75] Inventors: Witold Filipowicz, Riehen, Switzerland; Sheila Connelly, Gaithersberg, Md.

[73] Assignee: Novartis Finance Corporation, New York, N.Y.

[21] Appl. No.: 08/564,109

[22] PCT Filed: Jun. 15, 1995

[86] PCT No.: PCT/IB94/00155

§ 371 Date: Dec. 15, 1995

§ 102(e) Date: Dec. 15, 1995

[87] PCT Pub. No.: WO95/00652

PCT Pub. Date: Jan. 5, 1995

[30] Foreign Application Priority Data

Jun. 18, 1993 [CH] Switzerland .................. 1828/93

[51] Int. Cl.[7] .................. A01H 5/00; C12N 1/21; C12N 5/10; C12N 15/11
[52] U.S. Cl. .................. 800/295; 800/278; 800/279; 800/286; 800/289; 800/298; 800/300; 800/301; 800/302; 536/23.1; 536/23.6; 536/24.1; 435/69.1; 435/320.1; 435/418; 435/419; 435/430; 435/252.3
[58] Field of Search .................. 536/23.1, 23.6, 536/24.1; 435/69.1, 172.3, 320.1, 418, 419, 430, 254.11, 252.3; 800/205, 250, 278, 279, 286, 289, 295, 298, 300, 301, 302

[56] References Cited

U.S. PATENT DOCUMENTS

5,023,179 6/1991 Lam et al. .................. 435/172.3

FOREIGN PATENT DOCUMENTS

WO 89/01969 3/1989 WIPO .

OTHER PUBLICATIONS

Abstract No. 91–277587, Class B04, Database WP1, Section Ch, Week 9138, Foreign gene transcription and expression plasmid in which small nuclear RNA promoter is integrated:, *Derwent Publications Ltd.*,London, GB; (1991).

Bourque, et al., "Suppression of gene expression in plant cells utilizing antisense sequences transcribed by RNA polymerase III", *Plant Molecular Biology*, 19: 641–647 (1992).

Brown, et al., "Maize U2 snRNAs: gene sequence and expression", *Nucleic Acids Research*, 17: 8991–9001 (1989).

Connelly, et al., "Activity of Chimeric U Small Nuclear RNA (snRNA)/mRNA Genes in Transfected Protoplasts of *Nicotiana plumbaginifolia*: U snRNA 3'–End Formation and Transcription Initiation Can Occur Independently in Plants", *Molecular and Cellular Biology*, 13(10): 6403–6415 (1993).

Connelly, et al., "Requirements for 3' End Formation of Plant U–snRNA Transcripts and the Differential Expression of Monocot and Dicot U–snRNA Genes", *RNA Processing: Program and Abstracts*, Keystone, Colorado 81 (1992).

Edoh, et al., "Activity of U–snRNA genes with modified placement of promoter elements in transfected protoplasts and stably transformed tobacco", *Nucleic Acids Research*, 21(7): 1533–1540 (1993).

Goodall, et al., "The AU–Rich Sequences Present in the Introns of Plant Nuclear Pre–mRNAs Are Required for Splicing", *Cell*, 58: 473–483 (1989).

Goodall, et al., "Nuclear RNA Splicing and Small Nuclear RNAs and Their Genes in Higher Plants", *Plant Molecular & Cell Biology*, 7: 255–296.

Heard, et al., "Analysis of the Sequences and Factors Required for U–snRNA Gene Expression in Plants",*Journal of Cellular Biochemistry*, Supplmental 16E: 142 (1992).

Leader, et al., "Differential expression of U5snRNA gene variants in maize (*Zea mays*) protoplasts", *Plant Molecular Biology*, 21: 133–143 (1993).

Marshallsay, et al., "Structure, expression and evolution of plant U3 snRNA genes", *PhD thesis at the University of Basel*, (1991).

Patterson, et al., "An Essential Yeast snRNA with a U5–like Domain Is Required for Splicing In Vivo", *Cell*, 49: 613–624 (1987).

*Primary Examiner*—Elizabeth Kemmerer

[57] ABSTRACT

The present invention relates to a chimeric gene construction comprising one promoter element and a 3' termination signal in functional combination with a gene, wherein a) the promoter is an snRNA promoter element from plants specific for RNA polymerase II b) promoter element, of signalling the formation of RNA 3' ends, c)the gene codes for a polypeptide for sense RNA, for anti-sense RNA or for snRNA, with the proviso that, in the case of the snRNA, the 3' termination signal used in b) represents a eukaryotic poly(A) signal.

45 Claims, No Drawings

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 1:

TAATACGACT CACTATAGGG     20

(2) INFORMATION FOR SEQ ID NO: 2:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 2:

GGATCCGAAT TCAAAAGTTT CACTTCTAGT TTGGCGGGTT GAGCC          45

(2) INFORMATION FOR SEQ ID NO: 3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 3:

GGATCCGAAT TCAAAAGTTT CACTACTAGT TTGGCGGGTT GAGCC          45

(2) INFORMATION FOR SEQ ID NO: 4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 4:

GGATCCGAAT TCAAAAGGGG ACGGTCTAGT TTGGCGGGTT GAGCC          45

(2) INFORMATION FOR SEQ ID NO: 5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 5:

GGATCCGAAT TCAAAAGGGG ACGGTCTAGT TCCGCGGGTT GAGCC          45

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 6:

```
TTGAATTCAT TTAGACTAGT GTAAATGGCG GGTTGAGCCA GG                               42

(2) INFORMATION FOR SEQ ID NO: 7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

CTCAGAATTC AATTTTATTT TTTTGATTTG GCGGGTTGAG CCAGGCCCGT GCAG                  54

(2) INFORMATION FOR SEQ ID NO: 8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 8:

AATCTAGAGG ATCCCCGGGT ACCCTGTGAA TTGAACGAAT GGCTCAGC                         48

(2) INFORMATION FOR SEQ ID NO: 9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

ATGAATTCAC TAGTCCCACC TCGACAAGCT AGGG                                        34

(2) INFORMATION FOR SEQ ID NO: 10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 10:

ACTACTGGTA CCACTCGTGA GGTACGAGCG CTCGAGATGG G                                41

(2) INFORMATION FOR SEQ ID NO: 11:
```

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

GATTTAGGTG ACACTATAG                                                       19

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 12:

GGGATCGTTG GTCATAAGCT TTGTAG                                               26

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 13:

ATGAATTCAC TAGTCCCACA TCG                                                  23

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 14:

AATTCGCGGC CGCGGCGCCA ATGCATTGGG CCC                                       33

(2) INFORMATION FOR SEQ ID NO: 15:

(i) SEQUENCE CHARACTERISTICS:
        (A) LENGTH: 33 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 15:

AATTGGGCCC AATGCATTGG CGCCGCGGCC GCG                                33

(2) INFORMATION FOR SEQ ID NO: 16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 16:

CANNNAGTNN AA                                                       12

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 17:

NNNNNNNNNN RGCCCRNNNN NNNNNN                                        26

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 18:

NNNNNNNNNN YGGGCYNNNN NNNNNN                                        26
```

CHIMERIC PLANT GENES POSSESSING INDEPENDENT REGULATORY SEQUENCES

CROSS-REFERENCES TO RELATED APPLICATIONS

This application is filed under 35 U.S.C. § 371 from PCT/IB94/00155 (publication WO 95/00652), filed Jun. 15, 1994.

The present invention comes within the field of gene expression in plants and relates primarily to chimeric genes which contain an snRNA or mRNA promoter element and/or an snRNA 3' termination element from plants in functional combination with a structural gene, both elements being independent of each other in their function. In addition to this, the present invention relates to recombinant DNA vectors which comprise such chimeric gene constructs, and, furthermore, to microorganisms which harbour these vectors and to processes for preparing said chimeric gene constructs and vectors. Finally, the invention relates to plant cells, to parts of plants which can be regenerated to form whole and preferably fertile plants, and to the plants themselves including their descendents insofar as they express the chimeric genes according to the invention.

RNA polymerase II from eukaryotic cells transcribes two classes of genes: mRNA genes lead to the synthesis of mRNA, and snRNA genes to the synthesis of snRNA. The two classes of genes possess their own regulatory elements which differ from each other. The starting point or the initiation of transcription are determined and regulated by so-called promoter elements, and the end point of transcription or the formation of an intact RNA 3' end are signalled by so-called 3' termination elements.

In the cells of vertebrates, the 3' ends of the mRNA's are formed as a rule by endonucleolytic cleavage and subsequent polyadenylation of the primary RNA transcript. Here, the transcription for forming the primary transcript takes place first of all via a conserved AAUAAA hexanucleotide sequence and then via a subsequent G-U-rich or U-rich sequence. These two sequences are essential components of the so-called poly(A) signal that is responsible for the correct polyadenylation of the mRNA (Wahle and Keller, 1992).

Many yeast and plant mRNA's do not contain the hexanucleotide AAUAAA (Zaret and Sherman, 1984; Yu and Elder, 1989; Sanfacon et al., 1991; Mogen et al., 1992). However, it has been possible to show, using cell-free processing systems, that the mechanism of polyadenylation in yeast is analogous to the mechanism in vertebrate cells (Butler and Platt, 1988). The mechanism of polyadenylation of mRNA in plants is still not known.

In contrast to the formation of the 3' end of mRNA, formation of the 3' end of snRNA takes place simultaneously with transcription (Dahlberg and Lund, 1988; Hernandez and Lucito, 1988; Hernandez 1992). The site of transcription termination is signalled by the so-called 3' box, which is located beyond the gene sequence of the mature sRNA 3' end (Hernandez, 1985; Yuo et al, 1985).

It is a typical characteristic of all snRNA 3' termination elements in vertebrate cells that recognition of the 3' box signal is coupled to the initiation of transcription at the snRNA promoter element (Hernandez and Weiner, 1986; Neuman de Vegvar et al., 1986). This means that, in vertebrate cells, the promoter elements of snRNA genes also, at the same time, signal the formation of the correct 3' end. In the first place, these promoter elements contain approximately 200 bp of so-called "distal sequence elements" (DSE's) and approximately 60 bp of so-called "proximal sequence elements" (PSE's) prior to the transcription start point. In addition to this, these promoter elements are not able to initiate the transcription and synthesis of polyadenylated mRNA (Dahlberg and Schenborn, 1988). Due to these properties, snRNA genes cannot be expressed using an mRNA promoter element in vertebrate cells, for example.

It is known that an mRNA promoter element can successfully be used in yeast to transcribe an snRNA gene having a correct snRNA 3' end (Patterson and Guthrie, 1987). However, in yeast, the mRNA and snRNA promoters are virtually identical (Parker et al., 1988).

Plant snRNA genes, which are transcribed by RNA polymerase II, possess a 3' box having the consensus sequence CA(N)$_{1-3}$AGTNNAA (Goodall et al., 1991) SEQ ID NO.: 16 immediately downstream of the coding region. An important element of the present invention is based on the discovery that this 3' box, which, in plants as in vertebrate cells, plays an important part in the formation of the snRNA 3' end, surprisingly signals the formation of a correct snRNA 3' end irrespective of whether the transcription is initiated by an snRNA promoter element or an mRNA promoter element. In addition to this, transcripts whose synthesis is initiated by a plant snRNA promoter element can, surprisingly, be correctly spliced and polyadenylated Besides this, the initiation of transcription on an snRNA promoter element does not require the presence of an snRNA-encoding region and/or of a 3' box. Contrary to expectation, therefore, plant snRNA promoter elements can be used for expressing a very wide variety of expressible DNA sequences and genes. In this context, their ability to render constitutive expression possible in all plant cells is particularly advantageous, whereas the mRNA promoter elements which are customarily used are frequently either not expressed at all, or only expressed weakly in several cell types. The DNA sequences, which are required for realizing the invention, of the promoter and 3' box elements of monocotyledonous or dicotyledonous plants are either known or else can be isolated from appropriate gene banks using the known sequences and customary hybridization processes.

snRNA promoters which encompass a GC-rich regulatory DNA element of the formula Ia or Ib in one or more copies

| | |
|---|---|
| $(Np)_n RpGpCpCpCpR(pN)_m$ | (Ia)(SEQ ID NO.: 17) |
| $(Np)_n YpGpGpGpCpY(pN)_m$ | (Ib)(SEQ ID NO.: 18) | in which C is cytidine, G is guanosine, R is adenosine or guanosine, Y is cytidine or uridine, N is adenosine, guanosine, cytidine or uridine, p is a phosphate bridge between the 5' OH group and the 3' OH group of two nucleosides and n and m are a number between 0 and 10, preferably between 0 and 5, and particularly preferably between 0 and 2, as well as a functionally equivalent DNA element derived therefrom, are preferably used for the biotechnological expression of genes in monocotyledonous plants. This regulatory DNA element (Marshallsay, doctoral thesis), also termed an MSE element, is able to increase the activity of snRNA promoters in the chimeric genes according to the invention and represents a further subject of the invention.

BRIEF SUMMARY OF THE INVENTION

The present invention relates to a chimeric gene construct encompassing at least one promoter element and one 3' termination signal in functional combination with a structural gene, wherein a) at least one of the promoter elements is a plant snRNA promoter element or a structural and functional homologue thereof, preferably, however, is an RNA polymerase II-specific promoter element which optionally also encompasses one or more copies of the MSE element, and
b) the 3' termination signal is selected from a group of termination signals which are able to signal the formation of RNA 3' ends independently of the promoter element, for example eukaryotic poly(A) signals or 3' box elements of plant snRNA genes,
c) the structural gene codes for a polypeptide, which is expressed in a natural manner from an mRNA gene, for sense RNA including ribozymes, for anti-sense RNA or for snRNA, with the proviso that, in the case of snRNA, the 3' termination signal which is required in accordance with b) is a eukaryotic poly(A) signal.

In addition, the present invention relates to a chimeric gene construct encompassing a promoter element and a 3' termination signal in functional combination with a structural gene, wherein
a) the promoter is an mRNA promoter element or a structural and/or functional homologue thereof,
b) the 3' termination signal contains a plant snRNA 3' box or a structural and/or functional homologue thereof, and
c) the structural gene codes for snRNA, tRNA, rRNA, but preferably sense RNA or anti-sense RNA.

In the preferred embodiments of the invention, plant snRNA promoters and eukaryotic poly(A) signals are used in functional combination with different structural genes which, when expressed in the plant, confer advantageous properties on the latter. Within the scope of this invention, structural genes are preferred which make it possible to express selectable marker genes in plants, as are genes which code for proteins which protect the plants against pathogens, herbicides, fungicides, insecticides or disadvantageous environmental influences, as well as synthetic genes which code for one of the previously mentioned structural genes or other peptides, sense RNA or anti-sense RNA.

The invention additionally embraces recombinant DNA molecules which encompass, integrated into their DNA sequence, the said chimeric genes, processes for preparing the chimeric genes and plasmids using known chemical processes, recombinant DNA technology and molecular biology, as well as their use for transfecting herbaceous material, for example plant cells or plant protoplasts and whole plants as well.

Finally, the present invention also embraces plants, plant cells, plant parts which can be regenerated to form whole and preferably fertile plants, and their descendants, which harbour one of the chimeric gene constructs according to the invention. Thus, selectable marker genes, genes which code for proteins which protect the plants against pathogens, herbicides, fungicides, insecticides or disadvantageous environmental influences, as well as synthetic genes which code for one of the above mentioned structural genes or other peptides, for sense RNA or anti-sense RNA, can be expressed in plants.

The invention relates to a chimeric gene construction encompassing at least one promoter element and one 3' termination signal in functional combination with a structural gene, wherein
a) the promoter is a plant snRNA promoter element or a structural and/or functional homologue thereof,
b) the 3' termination signal is selected from a group of termination signals which are capable of signalling the formation of RNA 3' ends independently of the promoter element,
c) the structural gene codes for a polypeptide which is naturally expressed from an mRNA gene, for sense RNA, for anti-sense RNA or for snRNA, with the proviso that, for the latter case of the snRNA, the 3' termination signal which is required in accordance with b) is a eukaryotic poly(A) signal.

DETAILED DESCRIPTION OF THE INVENTION

The invention further relates to a chimeric gene construction encompassing a promoter element and a 3' termination signal in functional combination with a structural gene, wherein
a) the promoter is an mRNA promoter element or a structural and/or functional homologue thereof,
b) the 3' termination signal contains a plant snRNA 3' box or a structural and/or functional homologue thereof, and
c) the structural gene codes for snRNA, tRNA, rRNA, sense RNA or anti-sense RNA.

In this context, "functional combinations of promoter element and 3' termination signal with a structural gene is understood to mean the covalent linking of the said DNA elements. This linking results in a functional gene, that is one which is expressible in plants. The term "structural homologue" of a regulatory DNA sequence embraces all those DNA sequences which can be derived from the defined element by mutation. In this context, the homology with the defined element amounts to at least 60%, more preferably at least 80% and particularly preferably at least 90%.

The term "functional homologue" of a regulatory DNA sequence embraces all those DNA sequences whose regulatory function accords with the regulatory function of the defined element In this context, the magnitude of the regulatory effect is unimportant.

The preferences, which are listed below, for individual components of the invention, which components can, furthermore, be combined with each other in any particular form, are intended to assist in illustrating the diverse applicability of the chimeric genes according to the invention; however, they should not in any way be understood as limiting the subject matter of the invention.

Thus, as an example, a plant snRNA promoter element which is specific for RNA polymerase II is used in a preferred embodiment of chimeric genes. The promoters of the U snRNA genes for the splicing factors U1, U2, U4 and U5 are examples of RNA polymerase II-specific promoter elements.

In another preferred embodiment of chimeric genes, a plant snRNA promoter element is used which encompasses a GC-rich regulatory DNA element of the formula Ia or Ib in one or more copies

 (Ia)(SEQ ID NO.: 17)

 (Ib)(SEQ ID NO.: 18)

where C is cytidine, G is guanosine, R is adenosine or guanosine, Y is cytidine or uridine, N is adenosine, guanosine, cytidine or uridine, p is a phosphate bridge between the 5'-OH group and the 3'-OH group of two nucleosides and n and m are a number between 0 and 10, preferably between 0 and 5 and particularly preferably between 0 and 2, as well as a functionally equivalent DNA element derived therefrom.

Marker genes which code for proteins which are selectable or detectable in plants are used, for example, as structural genes of the chimeric genes according to the invention. Thus, the genes for resistance against kanamycin or G418, against methotrexate, hygromycin, bleomycin, aminoethylcysteine, glyophosphate, streptomycin, sulfonylurea, phosphinotricin and gentamicin, can, for example, be expressed, as can the genes for β-glucuronidase (GUS), chloramphenicol acetyltransferase (CAT) or luciferase.

Another group of structural genes which are preferably used are those which code for proteins which are able to protect plants against pathogens (for example phytopathogenic fungi, bacteria, viruses, etc.), herbicides (for example triazines, sulfonylureas, imidazolinones, triazolepyrimidines, bialaphos, glyophosates, etc.), fungicides, insecticides or disadvantageous environmental influences (for example heat, cold, wind, unfavourable soil conditions, moisture, dryness, etc.).

Within the scope of this invention, structural genes associated with the control of plant pathogens and parasites are particularly preferred.

For example, resistance towards insects can be transferred by a gene which codes for a polypeptide which is toxic for insects and/or their larvae, for example the crystalline protein of *Bacillus thuringiensis*. Such genes are known and described, for example, in U.S. Pat. No. 4,865,981, U.S. Pat. No. 4,996,155, WO 89/07605, EP 213,318 and EP 186,379.

The protease inhibitors are a second class of proteins which mediate insect resistance. Protease inhibitors form a normal constituent of plant storage structures and for this reason are usually located in vacuoles or "protein bodies". Thus, it was possible to demonstrate that the Bowman-Birk protease inhibitor, which was isolated and purified from soya beans, inhibits the intestinal protease of Tenebrio larvae (Birk et al., 1963). The gene, which codes for a trypsin inhibitor from the common cowpea, is described in Hilder et al. (1987).

Within the scope of the present invention, any protease inhibitor-encoding DNA sequences can now be used as structural genes, irrespective of their provenance (e.g. protease inhibitors from non-plant sources or from purely synthetic sources).

In this connection, mention must also be made of hydrolytic enzymes which are either able on their own to bring about degradation of the cell walls of plant pathogens or else are at least able to support this process, in a synergistic sense, in combination with other substances.

For example, the majority of insects possess a cuticular skeleton in which chitin micelles, layered in a lamellar fashion, are embedded in a ground substance. Numerous plant-pathogenic fungi, for example the basidiomycetes (smut and rust fungi), ascomycetes and *Fungi imperfecti* (including Alternaria and Bipolaris, *Exerophilum turcicum*, Colletotricum, Gleocercospora and Cercospora), also contain chitin as an integral constituent of their hyphal and spore structures. Chitinase is able to inhibit the mycelial growth of certain pathogens in vitro. A plant organ or tissue which is able to express chitinase constitutively or else as a response to penetration by a pathogen can thus protect itself against attack by a large number of different fungi.

Another enzyme which plays an important part in the mechanisms by which plants defend themselves against pathogens is β-1,3-glucanase. Genes which encode β-1,3-glucanase (GLB) are therefore preferably employed as structural genes for the chimeric genes according to the invention.

Of the genes which can mediate resistance to herbicides, the genes for 5-enolpyruvylshikimate-3-phosphate synthase (EPSP synthase), acetolactate synthase (ALS) and glutamine synthase (GS), and the PAT gene from streptomyces are preferred.

A further preferred embodiment of the chimeric genes according to the invention is represented by those which permit the expression of a synthetic gene which encodes a peptide or of a sense RNA or of an anti-sense RNA. In this context, the so-called lytic peptides are suitable peptides. These are natural or synthetic peptides which possess antipathogenic activity and which are able to penetrate, to lyse, or damage in some other way the pathogen cell membrane. Representatives of such lytic peptides which can be employed within the scope of the present invention are known both from animal (including insects) and plant and microbial sources and include, for example, the defensins, cercopins, thionins and mellitins of mammals, the defensins, magainins, attacins, dipterins, sapecins, caeruleins and xenopsins of insects, and hybrids thereof. The amino acid sequences of various lytic peptides are presented in the following publications: WO 89/11291; WO 86/04356; WO 88/05826; U.S. Pat. No. 4,810,777; WO 89/04371 as well as in Bohlmann et al. (1988), Selsted and Harwig (1987) and Terry et al (1988).

In the broadest sense, lytic peptides are also understood to mean compounds whose ability to penetrate, lyse or damage the cell membranes is based on an enzymic activity, for example lysozymes and phospholipases.

That which is particularly preferred within the scope of this invention is a combined expression of hydrolytic and lytic peptides. In addition to this, a reciprocal use of expression and exogenous application is also conceivable, with the lytic peptides, in particular, being suitable, for the latter purpose, in combination with the auxiliary substances and/or additives which are customarily used for this purpose.

An mRNA expressed in accordance with the invention does not necessarily have to encode a structural gene but can also be an mRNA which does not appear to possess any functional ORF, as described, for example, for the product of the mouse H19 gene (Brannan et al.) or the XIST gene (Brockdorff et al. and Brown et al.).

Of the 3' termination signals which are able, independently of the promoter element, to signal the formation of RNA 3' ends, those which deserve special mention are the eukaryotic poly(A) signals A such as the CaMV or the nos 3' termination signals, and functional homologues thereof.

Some typical examples of chimeric genes according to the invention are:

The Arabidopsis U2.2 promoter element and the CaMV poly(A) signal in functional combination with a structural gene of a marker protein which is selectable in plants The Arabidopsis U2.2 promoter element and the CaMV poly(A) signal in functional combination with a structural gene which is able to protect plants against pathogens, herbicides, fungicides, insecticides or disadvantageous environmental influences.

The Arabidopsis U2.2 promoter element and the CaMV poly(A) signal in functional combination with a structural gene which encodes a natural or synthetic peptide.

The 35S or 19S Cauliflower Mosaic Virus promoter element and the Arabidopsis U2.2 3' box in functional combination with a synthetic structural gene which encodes sense RNA or anti-sense RNA.

The β-1,3-glucanase promoter element and the Arabidopsis U2.2 3' box in functional combination with a synthetic structural gene which encodes sense RNA or anti-sense RNA.

The nopaline synthase or octopine synthase promoter element and the Arabidopsis U2.2 3' box in functional combination with a synthetic structural gene which encodes sense RNA or anti-sense RNA.

Examples of other regulatory DNA sequences which can be employed for constructing chimeric genes are sequences which are able to regulate the transcription of an associated DNA sequence in plant tissues in the sense of an induction or repression.

Thus, there are, for example, individual plant genes which are known to be induced by various internal and external factors such as plant hormones, heat shock, chemicals, pathogens, oxygen lack, light, stress, etc.

Abscissic acid (ABA), which is known to induce the excess of mRNA's which occurs in cotton during the late embryonic phase, can be mentioned here as an example of gene regulation by a plant hormone. A further example is provided by gibberellic acid (GA3) which induces malate synthase transcripts in ricinus seeds and α-amylase isoenzymes in the aleurone layers of barley.

The activities of glucanase and chitinase can be markedly increased in bean leaves by treatment with the stress hormone ethylene. In the case of chitinase, this induction effect is controlled by way of the chitinase gene promoter as has been demonstrated by reporter gene experiments using a chitinase gene promoter from beans (*Phaseolus vulgaris*).

The regulation of soya bean protein genes which are sensitive to heat shock was investigated in detail. Treatment of the plants for several hours at a temperature of 40° C. results in the de novo synthesis of so-called heat shock proteins. A large number of these genes have by now been isolated and their regulation analysed in detail. Expression of these genes is primarily controlled at the level of transcription. If, for example, the promoter of the hps70 gene is fused to the neomycin phosphotransferase II (NPT II) gene, the chimeric gene produced in this way can then be induced by a heat shock (Spena et al., 1985).

Another class of inducible plant genes comprises the light-regulated genes, in particular the gene, encoded in a nucleus, for the small subunit of ribulose-1,5-bisphosphate carboxylase (RUBISCO). Morelli et al. (1985) have demonstrated that the 5' flanking sequence of a pea RUBISCO gene is able to confer light-inducibility to a reporter gene if the latter is linked in chimeric form with this sequence. It was also possible to extend this observation to other light-induced genes, for example the chlorophyll a/b binding protein.

The alcohol dehydrogenase genes (adh genes) of maize have been the subject of intensive investigations. The maize adh 1-s gene has been isolated and it has been demonstrated that a part of the 5' flanking DNA is able to induce expression of a chimeric reporter gene (e.g. chloramphenicol acetyltransferase; CAT) if the transiently transformed tissue is exposed to anaerobic conditions (Howard et al., 1987).

A further group of regulatable DNA sequences concerns chemically regulatable sequences which are present, for example, in the tobacco PR ("pathogenesis-related") protein genes and are inducible using chemical regulators (EP-A 332 104).

The regulatable DNA sequences, which were mentioned previously by way of example, can be of either natural or synthetic origin or else comprise a mixture of natural and synthetic DNA sequences.

It is furthermore advantageous if the expressible DNA, in particular the structural gene to be inserted, contains a sequence, or else is linked to such a sequence by its 5' terminal region, which codes for an N-terminal signal peptide which is capable of functioning in the plant cell. This signal peptide is a transport signal which is located at the N-terminal end of proteins which are transported via the endomembrane system. This signal sequence ensures that the said proteins initially gain entry into the endoplasmic reticulum, where the signal peptide is proteolytically cleaved from the precursor protein as soon as it has fulfilled its function. In conformity with its specific function, this type of sequence possessed by the signal peptide has to a large extent been conserved in all living cells during the course of evolution, regardless of whether they are bacterial, yeast, fungal, animal or plant cells.

On the other hand, at the C-terminal end of vacuolar proteins, sequences can be found which mediate the transport of the associated structural gene into the vacuole. Examples of such sequences are described, for example, in EP-A 462 065.

Finally, the expressed DNA can also contain sequences which encode peptide fragments which improve the transport of a gene into the vacuoles (Matsuoka, K. and K. Nakamura, 1991).

Additional regulatory segments of the sequence of the 5' non-translated region encompass, for example, so-called "enhancer" sequences which can bring about an increase in expression rates and which can be obtained, for example, from the upstream region of the maize alcohol dehydrogenase 1 gene (Adh 1 gene) or of the octopine synthase gene. These "enhancer" sequences, for example the anaerobic regulatory element, the octopine synthase element or intron 1 from the Adh 1 gene, can be employed individually, as repetitions, or else combined among themselves, as described, for example, in EP-A 459 643 using the native 35S CaMV promoter.

The invention also relates to a plasmid possessing the ability to replicate in a microorganism, principally in *E. coli*, Bacillus, Agrobacterium or yeast, which plasmid contains a chimeric gene according to the invention integrated in its DNA sequence. In a particularly preferred embodiment, this plasmid is a shuttle vector which is capable of replicating both in agrobacterium and in one of the microorganisms selected from the group *E. coli*, Bacillus and yeast. In another preferred embodiment, the plasmid is a binary Ti or Ri vector.

Within the scope of this invention, therefore, a system for transferring a T DNA region from Agrobacterium into plant cells is preferably used in which the vir region and the T DNA region are located on different vectors. Such a system is known under the term "binary vector system" and the vector containing the T DNA is correspondingly termed a "binary vector" while the plasmid containing the vir region is, as a rule, referred to as the "helper" plasmid.

Examples of binary vectors which can be used within the scope of this invention are the plasmid pCIB200 described in EP-A 332 104 or the plasmids pGA482 and pGA580 which can be obtained from PHARMACIA.

Any T DNA-containing vector which can be transferred into plant cells and which permits selection of the transformed cells is suitable for use within the scope of this invention.

The present invention also embraces a process for preparing the chimeric genes according to the invention, wherein methods of organochemical polynucleotide synthesis, which are known per se, are either used on their own or in combination with recombinant DNA methods which are known per se. Within the methods of organochemical polynucleotide synthesis, three different process variants are nowadays distinguished, all of which can be used within the scope of this invention. These processes are the phosphodiester, the phosphotriester and the phosphoramidite methods.

The syntheses in accordance with the previously described processes yield single-stranded DNA fragments which must subsequently be converted into double strands. In most cases, known recombinant DNA methods, as described, for example, in Sambrook et al., 1989, are then also employed for producing the DNA double strands. In this connection, the polymerase chain reaction method, in particular, has gained increasing importance in recent years.

In addition to this, the present invention embraces a process for preparing plasmids which contain the chimeric genes according to the invention incorporated in their DNA sequence, in which process a) the individual elements of the chimeric gene are covalently bonded to each other in the desired plasmid vector using recombinant DNA methods,
b) the resulting plasmid is transformed into a microorganism, and
c) the plasmid is subsequently isolated from transformed microorganisms after they have been lysed, and purified.

The methods and processes which are used in the course of the three procedural steps a) to c) are known per se and are described, for example, in Sambrook et al., 1989. *E. coli*, Bacillus, Agrobacterium or yeast are employed, in particular, for the microorganism transformation in accordance with procedural step b).

Microorganisms which harbour and replicate one of the plasmids according to the invention are a further subject of the invention.

The chimeric genes and plasmids according to the invention may be used in many ways. In this context, their use for transfecting plant cells and for expressing, in all plant cells, structural genes, which are expressed in a natural manner from an mRNA promoter, is of particular interest.

By now, there exist a series of very efficient processes for inserting DNA into plant cells which are based on the use of transfer vectors or on direct gene transfer processes. The insertion of the chimeric genetic constructs according to the present invention is preferably effected into plant protoplasts using known gene transfer processes.

One option for transformation consists, for example, in bringing plant cells into contact with viruses or with Agrobacterium.

Thus, the entire genome of the Cauliflower Mosaic Virus (CaMV), together with a chimeric gene according to the invention, can be integrated into a bacterial parent plasmid using recombinant DNA methods.

The modified viral portion of the recombinant plasmid, which also contains the chimeric gene, can then be excised from the bacterial parent plasmid and used for inoculating the plant cells or the whole plants.

Another method for inserting the chimeric gene constructs into the cell makes use of infection of the plant cell with *Agrobacterium tumefaciens* and/or *Agrobacterium rhizogenes*, with the Agrobacteria replicating plasmids which contain the chimeric genes according to the invention.

Within the area of Agrobacterium-mediated transformation, so-called leaf-disc transformation has proved to be a particularly efficient process (Horsch et al., 1985). In this process, sterile leaf discs from a suitable target plant are incubated with Agrobacterium cells which harbour one of the chimeric gene constructions according to the invention and are subsequently transferred into or onto a suitable nutrient medium. Those media which are particularly suitable, and therefore preferred within the scope of this invention, are LS media which are solidified by adding agar and which are enriched with one or more of the customarily used plant growth regulators, in particular, however, those selected from the auxin group comprising a-naphthylacetic acid, picloram, 2,4,5-trichlorophenoxyacetic acid, 2,4-dichlorophenoxyacetic acid, indole-3-butyric acid, indole-3-lactic acid, indole-3-succinic acid, indole-3-acetic acid and p-chlorophenoxyacetic acid, as well as from the cytokinin group comprising kinetin, 6-benzyladenine, 2-isopentenyladenine and zeatin. The preferred concentrations of the auxins and cytokinins are within a range from 0.1 mg/l to 10 mg/l.

After an incubation lasting several days, but preferably lasting from 2 to 3 days, at a temperature of from 20° C. to 40° C., preferably of from 23° C. to 35° C., and very particularly preferably of 25° C., and under a diffuse light, the leaf discs are transferred to a suitable medium for shoot induction. The medium which is particularly preferred for selecting the transformants is a LS medium which, while it does not contain any auxin does contain a cytokinin, and has been treated with a selective substance. The cultures are maintained in the light and, at suitable intervals, preferably, however, at intervals of one week, are transferred to fresh medium. Green shoots which develop are cut out and then subjected to further cultivation in a medium which induces rooting of the shoots. Within the scope of this invention, an LS medium is particularly preferred which does not contain any auxin or cytokinin but which is treated with a selective substance for selecting the transformants.

Within the scope of this invention, direct transformation processes may also be used, as well as Agrobacterium-mediated transformation, for inserting the gene constructions according to the invention into plant material.

Thus, the genetic material which is contained in a vector can, for example, be inserted directly into the plant cell using purely physical measures, for example by microinjection using finely drawn-out micropipettes (Neuhaus et al., 1987) or by bombarding the cells with microprojectiles which are coated with the transforming DNA ("Microprojectile Bombardment"; Wang Y-C et al., 1988). More recent developments in this area relate to devices which accelerate the microprojectiles, under high pressure, through a DNA-containing solution in the direction of the cell material to be transformed, the said solution being atomized in very fine droplets (EP-A 434,616). Thus, maize plants, for example, can be successfully transformed using microprojectile bombardment (EP-A 478 502).

Further options for the direct transfer of genetic material into the plant cell consist in the treatment of the protoplasts with procedures, for example polyethylene glycol treatment, heat-shock treatment or electroporation, or a combination of these procedures (Shillito et al., 1985), which modify the plasma membrane.

In the electroporation technique, plant protoplasts together with plasmids encompassing the chimeric gene construction are subjected to electrical impulses of a high field strength. This leads to a reversible increase in the permeability of biomembranes and thus makes it possible to insert the plasmids. Electroporated plant protoplasts renew their cell walls, divide and form callus tissue. The transformed plant cells can be selected using the previously described phenotypic markers. The direct electroporation of intact plant cells or tissues is preferred, prior to which electroporation the cells or tissues are not subjected to any pretreatment.

A further process for directly introducing genetic material into plant cells, which process is based on purely chemical procedures and makes it possible to carry out the transformation very efficiently and rapidly, is described in Negrutiu I et al. (1987).

Direct gene transfer using co-transformation (Schocher R J et al. 1986) is likewise suitable for transforming plant material. Co-transformation is a method which is based on the simultaneous uptake and integration of different DNA molecules (non-selectable and selectable gene) into the plant genome, and which therefore makes it possible to identify cells which are transformed with non-selectable genes.

The above list, given by way of example, of possible transformation processes does not make any claim to be complete and is not intended to restrict the subject matter of the invention in any way.

Those cell clones which contain the chimeric gene constructs incorporated into their genomes are picked out using customary selection, screening and detection methods and may be used for regenerating transgenic plants.

The regeneration of culture-maintained protoplasts to form whole plants is described, for example, in Potrykus I and Shillito RD (1986).

The regeneration processes differ from plant species to plant species. In general, however, the protoplasts are stimulated to divide and to form cell walls in one of the known culture media. Finally, callus cultures arise which can be induced to form roots and/or shoots by treatment with particular active compounds, for example auxins and cytokinins.

The plantlets thus obtained can subsequently be transferred into soil and cultivated further in the same way as normal seedlings.

The transgenic plants which have been regenerated from protoplasts, cells, calluses, tissues, organs, seeds, embryos, pollen, egg cells, zygotes, etc., and which harbour, as an integral constituent of the plant genome, a structural gene, which can be expressed in the plant cell, of the previously described chimeric gene construction can be replicated vegetatively, preferably in the form of sterile shoot cultures.

The present invention consequently also relates to plant parts, for example protoplasts, cells, calluses, tissues, organs, seeds, embryos, pollen, egg cells, zygotes, etc., which can be regenerated into whole and preferably fertile plants, as well as, in particular, to whole and preferably fertile plants which have been transformed using the previously described processes and which express chimeric genes according to the invention.

Within the scope of this invention, transgenic plants, including their sexual and asexual descendants, are preferred which can be regenerated from plant material selected from the group consisting of protoplasts, cells, calluses, tissues, organs, seeds, embryos, pollen, egg cells, zygotes, etc., and which express one of the chimeric genes according to the invention.

All mutants and variants which can be obtained using known processes, for example by cell fusions or mutant selection, and which still display the characteristic properties of the transformed starting plant, as well as all products obtained by crossing and fusing the transformed plant material, fall, by definition within the scope of this invention, within the term asexual and/or sexual descendants of transgenic plants.

The plants which have been transformed using the above-mentioned transformation processes, and which are a further subject of the invention, are those of the systematic groups Angiospermae and Gymnospermae.

Among the Gymnospermae, the plants of the Coniferae class a re of particular interest.

Among the Angiospermae, in addition to the deciduous trees and shrubs, plants of the families Solanaceae, Cruciferae, Compositae, Liliaceae, Vitaceae, Chenopodiaceae, Rutaceae, Alliaceae, Amaryllidaceae, Asparagaceae, Orchidaceae, Palmae, Bromeliaceae, Rubiaceae, Theaceae, Musaceae, Malvaceae or Gramineae, and of the order Leguminosae, and here, especially, of the family Papilionaceae, are of particular interest. Representatives of the families Solanaceae, Cruciferae and Gramineae are preferred.

Within the scope of the present invention, the target cultures also include, for example, those selected from the series: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Gossypium, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum, Ipomoea, Passiflora, Cyclamen, Malus, Prunus, Rosa, Rubus, Populus, Santalum, Allium, Lilium, Narcissus, Ananas, Arachis, Phaseolus and Pisum.

As a result of novel developments in the field of the in-vitro cultivation of plants, especially in the field of plant regeneration, it has, in the meantime, become possible also to regenerate whole plants in the case of representatives of the Gramineae family, starting from plant protoplasts. Examples of regeneration experiments which have been successfully carried out using Gramineae are described, inter alia, in Yamada Y et al. (1986) for rice protoplasts, in Rhodes et al. (1988) and Shillito RD et al. (1989) for maize protoplasts, and in Horn et al. (1988) for *Dactylis glomerata* protoplasts.

Within the scope of the present invention, the following plants can also be used: Lolium, Zea, Triticum, Sorghum, Saccharum, Bromus, Oryzae, Avena, Hordeum, Secale and Setaria.

Following the general description of the present invention, reference will now be made, for improved comprehension, to specific implementation examples which are included in the description for the purposes of illustration and which have no limiting character unless this is specifically indicated.

EXAMPLES

The methods and techniques required for constructing the plasmids described below are known from the literature and are described, for example, in Sambrook et al., 1989. In this context, plasmids are obtained, as a rule, by ligating from 1 to 4, preferably 1–3, DNA fragments. The different ligation products are subsequently transformed into *E. coli* cells. These cells are then cultivated under selective conditions so that only those bacteria survive which were transformed with a plasmid which expresses a resistance gene. The plasmids of bacterial clones selected in this way can now be isolated and analysed using restriction enzymes. Those clones which harbour the desired plasmids are then subsequently used for preparing the plasmid DNA. For the sake of clarity, the above-described procedures are not repeated in the description, which now follows, of the processes for preparing plasmids according to the invention. Instead, the presentation is limited to describing the DNA fragments used for the ligations.

Fragments which are required for a ligation are frequently prepared by means of the polymerase chain reaction (Saiki et al., 1988). In detail, the approach is initially to synthesize short "primer" sequences which are in each case located at the ends of the DNA region to be amplified and which, owing to the sequence homologies which are present, are able to hybridize with the corresponding sequence segments. If the DNA to be amplified is present in the double-stranded form, it must initially be disassociated into single strands by heat treatment. After the primers have been annealed on, the single strands are filled in to form the double strand in a DNA polymerase-catalysed reaction in the presence of dNTP's.

This reaction cycle, consisting of denaturation, annealing-on of the primers and polymerization to form the double strand, can be repeated as often as required, leading finally to a million-fold enrichment of the DNA region lying between the primers. By using thermostable DNA polymerases, for example the heat-stable polymerase from the thermophilic bacterium Thermus aquaticus (so-called Taq polymerase), which are still active at temperatures of greater than 70° C. and are consequently not destroyed by heat-denaturation, the previously mentioned reaction steps can all be carried out in the same reaction mixture. In this procedure, the temperatures for annealing-on the primers depend on the primer sequences and are between 37° C. and 72° C.

A) Preparation and Transfection of Protoplasts

A1) *Nicotiana plumbaginifolia* protoplasts 6 leaves from a 6–8 week-old shoot culture are cut into approximately 1 mm-wide strips and incubated overnight at 25° C. in 12 ml of a freshly prepared enzyme solution. This solution contains 0.5% driselase, 0.25% polyvinylpyrrolidone, 0.5 M sucrose, 3.85 mM $CaCl_2$, 6 mg/ml NAA and 2 mg/ml BAP and is stirred for 30 minutes before use and subsequently filtered to render it sterile. After having been incubated overnight, the cells are suspended by careful shaking and the cell suspension is filtered through a 100 gm filter. The protoplasts are isolated from the filtrate by ultracentrifugation using a solution (W5) consisting of 154 mM NaCl, 5 mM KCl, 125 mM $CaCl_2$ and 5 mM glucose adjusted to a pH of 6.0. Prior to transfection, the protoplasts are centrifuged off and suspended, to a concentration of $2 \times 10^6$ cells/ml, in a solution (MC) of 5 mM MES, 20 mM $CaCl_2$ and 0.5 mM mannitol adjusted to a pH of 5.7.

A2) *Nicotiana plumbaginifolia* transfection using PEG

15 µg of plasmid DNA are mixed together with $6 \times 10^5$ protoplasts from Example A1. 300 µl of a 40% solution of PEG 6000 are added and this is followed by careful mixing with the mixture subsequently being incubated at room temperature for 1–5 minutes. Finally, the protoplasts are taken up in 4 ml of culture medium K3M (Goodall et al., 1990), which additionally contains 0.001% Tween 80 and 0.45 M glucose, and transferred into 15 ml plastic tubes which are now incubated in the dark at 26° C. for 24 hours.

B) RNAse A/T1 Mapping

RNAse A/T1 mapping is used for quantitatively analysing the splice pattern of transcripts. RNA is isolated from transfected protoplasts and hybridized with uniformly $^{32}P$-labelled RNA probes. This is then followed by incubation with a mixture of RNAse A and RNAse T1. In the RNA hybrids, the intron sequences of the labelled RNA probes are not protected by base pairing with the spliced RNA and are therefore degraded by the RNAses. The resulting $^{32}P$-labelled fragments, which are now shorter, correspond to the Exon sequences. The precise methods for isolating RNA from transfected protoplasts, for preparing uniformly $^{32}P$-labelled RNA probes and for RNAse A/T1 mapping are known and are described in Goodall et al., 1990. The plasmids from Examples B1 and B2 are used for synthesizing $^{32}P$-labelled RNA probes.

B1) Preparation of the plasmid pGEM2/cDNA

The plasmid obtained in Example E4 and the commercially available vector pGEM®2 are cut, separately from each other, using the restriction enzymes XbaI and PstI. The 90 bp-sized fragment containing the synthetic cDNA of the plasmid from Example E4 and the fragment of approximately 2.8 kb in size from the vector pGEM®2 are isolated and ligated to each other. The title plasmid pGEM2/cDNA, which contains one copy of each of the two fragments, is obtained.

B2) Preparation of the plasmid pGEM2/Kpn

The plasmid obtained in Example F1 is cut with the restriction enzyme KpnI and the 3' protruding DNA ends thereby produced are removed and bluntended using T4 DNA polymerase. The 455 bp-sized fragment of the plasmid from Example F1, containing the U2-coding region including 3' box and the CaMV polyA signal, and the pGEM®2 vector, which has been linearized with SmaI and dephosphorylated, are isolated and ligated to each other. The title plasmid pGEM2/Kpn, which contains one copy of each of the two fragments, is obtained.

C) Importance of the 3' Box for Forming snRNA 3' Ends

C1) Preparation of the plasmid U2PCR

An approximately 0.6 kb-sized fragment, containing the Arabidopsis U2.2 gene, is amplified, in a polymerase chain reaction (PCR), from the plasmid pGEM®2.U2.2 (Vankan and Filipowicz, 1989) using a 5' oligonucleotide (20 mer 5'-TAATACGACT CACTATAGGG-3'; SEQ ID NO: 1), which is complementary to the T7 promoter, and a 3' oligonucleotide (45 mer, 5'-GGATCCGAAT TCAAAAGTTT CACTTCTAGT TTGGCGGGTT GAGCC-3', SEQ ID NO: 2) which is complementary to the 3' end of the Arabidopsis U2.2 gene. The resulting fragment, like the pGEM02 vector, is cut with BamHI and EcoRI. The isolated fragments, of approximately 0.6 kb and 2.8 kb in size, are ligated to each other. The title plasmid U2PCR, which contains one copy of each of the two fragments, is obtained.

C2) Preparation of the plasmid U2SPE

The preparation is carried out in analogy with Example C1, with a modified 3' oligonucleotide being used (45 mer 5'-GGATCCGAAT TCAAAAGTTT CACTACTAGT TTG-GCGGGTT GAGCC-3', SEQ ID NO: 3). This results in a SpeI cleavage site being introduced at the 3' end of the amplified fragment. The title plasmid U2SPE is obtained.

C3) Preparation of the plasmid U2ΔDS1

The plasmid obtained in Example C2 is cut using the restriction enzymes EcoRI and SpeI and the 5' protruding ends arising as a result are filled in and blunt-ended using the Klenow fragment of *E. coli* DNA polymerase I in the presence of deoxynucleotide triphosphates. The fragment of approximately 3.4 kb in size is subsequently isolated and closed once again to form a ring-shaped molecule by intramolecular ligation. The title plasmid U2ΔDS 1, whose 3' box is mutated at five positions, is obtained.

C4) Preparation of the plasmid ΔDS2

The preparation is carried out in analogy with Example C1, with a modified 3' oligonucleotide being used (45 mer, 5'-GGATCCGAAT TCAAAAGGGG ACGGTCTAGT TTGGCGGGTT GAGCC-3', SEQ ID NO: 4). This results in the sequence 5'-AGTGAAA-3' in the 3' box of the amplified fragment being replaced by the sequence 5'-CCGTCCC-3'. The title plasmid ΔDS2 is obtained.

C5) Preparation of the plasmid ΔDS2/CA→GG

The preparation is carried out in analogy with Example C1, with a modified 3' oligonucleotide being used (45 mer, 5'-GGATCCGAAT TCAAAAGGGG ACGGTCTAGT TCCGCGGGTT GAGCC-3', SEQ ID NO: 5). This results in the CA dinucleotide at the beginning of the 3' box of the amplified fragment being replaced by the dinucleotide GG and the sequence AGTGAAA at the end of this 3' box being replaced by the sequence CCGTCCC. The title plasmid ΔDS2/CA→GG is obtained.

C6) Gene expression using the plasmids from Examples C1 to C5

Expression of the plasmids from the Examples C1 to C5 in transfected plant protoplasts is investigated using RNAse A/T1 mapping:

U2PCR and U2SPE express equal quantities of U2 snRNA. By definition, their expression amounts to 100% of U2. By comparison, U2ΔDS1 and ΔDS2, which contain 5 and 7 mutations, respectively, in their 3' box, only express 15–20% of U2 snRNA. In plasmid ΔDS2/CA→GG, the CA dinucleotide of the 3' box is mutated into GG in addition to the 7 ΔDS2 mutations. The expression of U2 snRNA is only 6% of the control value. The results demonstrate that the 3' box is necessary for the expression of snRNA.

D) The 3' Boxes of Different snRNA Genes are Interchangeable

D1) Preparation of the plasmid AU2/AU5

The preparation is carried out in analogy with Example C1, with a modified 3' oligonucleotide being used (42 mer, 5'-TTGAATTCAT TTAGACTAGT GTAAATGGCG GGT-TGAGCCA GG-3', SEQ ID NO: 6). This results in the Arabidopsis U2.2 3' box being replaced by an Arabidopsis U5 3' box (Vankan et al. 1988). The title plasmid AU2/AU5 is obtained.

D2) Preparation of plasmid AU2/MU2

The preparation is carried out in analogy with Example C1, with a modified 3' oligonucleotide being used (54 mer, 5'-CTCAGAATTC AATTTTATTT TTTTGATTTG GCGGGTTGAG CCAGGCCCGT GCAG-3', SEQ ID NO: 7). This results in the Arabidopsis U2.2 3' box being replaced by a maize U2 3' box (Brown and Waugh 1989). The title plasmid AU2/MU2 is obtained.

D3) Gene expression using the plasmids from Examples D1 and D2

The expression of the plasmids from the Examples DI and D2 in transfected plant protoplasts is investigated using RNAse A/T1 mapping:

Both AU2/AU5 and AU2/MU2 express approximately the same amount of U2 snRNA as does U2PCR. The different 3' box elements are therefore interchangeable.

E) The snRNA Promoter Permits the Synthesis of Polyadenylted RNA

E0) Preparation of the plasmid pDEDH-SP6

Plasmid pDEDH (Goodall and Filipowicz, 1989) is cut using the restriction enzyme SacI and the 3' protruding ends arising as a result are removed and blunt-ended using T4 DNA polymerase. Subsequently, the DNA is also cut with EcoRI and the 1.5 kb DNA fragment is isolated which contains the CaMV promoter and the CaMV poly(A) signal. At the same time, the commercially available vector pSP64 is converted into a linear DNA molecule using the restriction enzyme HindIII and the 5' protruding ends arising as a result are filled in and blunt-ended using the Klenow fragment of E. coli DNA polymerase I in the presence of deoxynucleotide triphosphates. Subsequently, the DNA is also cut with EcoRI. The 3 kb-sized pSP64 fragment and the 1.5 kb fragment from plasmid pDEDH are ligated to each other. The title plasmid pDEDH-SP6, which contains one copy of each of the two fragments, is obtained.

E1) Preparation of the plasmid CaMVp/syn

A 180 bp-sized DNA fragment having an end cut with XbaI and an end cut with PstI is isolated by restriction digestion from the plasmid pGS7 (Goodall and Filipowicz, 1989). This fragment encodes a synthetic gene comprising exon 1, intron and exon 2. The plasmid obtained in Example E0 is likewise cut with XbaI and PstI and the fragment of approximately 4.5 kb in size is isolated. The title plasmid CaMVp/syn, which contains one copy of each of the two fragments, is obtained by ligating the two fragments.

E2) Preparation of the plasmid U2p/syn

The Arabidopsis U2.2 promoter element is amplified, in a polymerase chain reaction (PCR), from the plasmid pGEM2.U2.2 (Vankan and Filipowicz, 1989) using a 5' oligonucleotide (20 mer, 5'-TAATACGACT CACTATAGGG-3'; SEQ ID NO: I) and a 3' oligonucleotide (48 mer, 5'-AATCTAGAGG ATCCCCGGGT ACCCTGT-GAA TTGAACGAAT GGCTCAGC-3'; SEQ ID NO: 8). In this case, the 5' oligonucleotide is complementary to the T7 promoter and the 3' oligonucleotide complementary to the promoter of the Arabidopsis U2.2 gene. In addition, the 3' oligonucleotide contains, at its 5' end, 24 nucleotides which are complementary to the synthetic gene of the plasmid from Example E1. The amplified fragment is next cut with BamHI and the resulting 5' protruding ends are filled in and blunt-ended using Klenow polymerase. Subsequently, the DNA is also cut with SmaI. The plasmid from Example E1 is then cut with EcoRI and the resulting 5' protruding ends are filled in and blunt-ended using Klenow polymerase. After that, the DNA is also cut with SmaI and the large fragment is isolated. This latter fragment is then ligated to the PCR fragment. The title plasmid U2p/syn, which contains one copy of each of the two fragments, is obtained.

E3) Preparation of the plasmid U2pMUT/syn

The preparation is carried out in analogy with Example E2, with a modified 5' oligonucleotide (34 mer, 5'-ATGAATTCAC TAGTCCCACC TCGACAAGCT AGGG-3'; SEQ ID NO: 9) being used. This results in a mutation from A to C, which reduces the promoter strength to 20% (Vankan and Filipowicz, 1989), being introduced in the USE part of the Arabidopsis U2.2 promoter element. The title plasmid U2pMUT/syn is obtained.

E4) Preparation of the plasmid CaMVp/cDNA

In order to produce the cDNA corresponding to the synthetic gene from Example E1, the intron is removed using the polymerase chain reaction. For this purpose, a 5' oligonucleotide (41 mer, 5'-ACTACTGGTA CCACTCGTGA GGTACGAGCG CTCGAGATGG 0-3'; SEQ ID NO: 10) and a 3' oligonucleotide (19 mer, 5'-GATTTAGGTG ACACTATAG; SEQ ID NO: 1 1) are used with the 5' oligonucleotide encompassing a KpnI restriction cleavage site flanking the intron. The product of the polymerase chain reaction is cut with the restriction enzymes KpnI and PstI and ligated into plasmid pGS7 cut with KpnI and PstI. The fragment corresponding to the cDNA is isolated from the resulting plasmid, following restriction digestion with XbaI and PstI and ligated into the XbaI and PstI cleavage sites of the plasmid from Example E1, resulting in the synthetic gene being replaced by the cDNA. The title plasmid CaMVp/cDNA is obtained.

E5) Preparation of the plasmid U2p/cDNA

The plasmid is prepared in analogy with Example E4 using the same oligonucleotides. However, the plasmid from Example E2 is used instead of the plasmid from Example E1. The title plasmid U2p/cDNA is obtained.

E6) Gene expression using the plasmids from Examples E1 to E5

Expression of the synthetic gene in U2p/syn, investigated using RNAse A/T1 mapping, is approximately 40%, and that in U2pMUT/syn approximately 20%, of the expression in CaMVp/syn. In the case of U2p/syn or U2pMUT/syn, 65% of the RNA is polyadenylated, while 90% is polyadenylated in the case of CaMVp/syn.

RNA expressed from the synthetic cDNA of the plasmid CaMVp/cDNA is polyadenylated to the extent of 83% and RNA expressed from plasmid U2p/cDNA to the extent of 63% snRNA gene promoters thus permit the synthesis of polyadenylated RNA.

F) Expression of Different Chimeric Genes Having a Polyadenylation Signal

F1) Preparation of the plasmid U2/pA

The plasmid from Example E0 is cut with EcoRI and BamHI and the 5' protruding ends are subsequently filled in and blunt-ended using Klenow polymerase. The vector fragment is isolated Plasmid pGEM2.U2.2 (Vankan and Filipowicz, 1989) is likewise cut with EcoRI and BamHI and the 5' protruding ends are filled in and blunt-ended using Klenow polymerase. The fragment possessing the U2-encoding region is isolated. The two fragments are ligated to each other and the title plasmid U2/pA, which contains one copy of each of the two fragments, is obtained.

F2) Preparation of the plasmid U2/3'MUT/PA

The preparation is carried out in analogy with Example F1 but using the plasmid from Example C5 instead of the plasmid pGEM2.U2.2. The title plasmid U2/3'MUT/pA is obtained.

F3) Preparation of the plasmid CaMVp/U2/pA

A fragment which contains the U2-encoding region is amplified, in a polymerase chain reaction (PCR), from the plasmid pU2.2/ClaI (Vankan and Filipowicz, 1989) using a 5' oligonucleotide (26 mer, 5'-GGGATCGTTG GTCAT-AAGCT TTGTAG-3'; SEQ ID NO: 12) and a 3' oligonucleotide (45 mer, 5'-GGATCCGAAT TCAAAAGTTT CACT-TCTAGT TTGGCGGGTT GAGCC-3'; SEQ ID NO: 2). In this case, the 5' oligonucleotide is complementary to the U2.2 promoter region and the 3' oligonucleotide complementary to the 3' end of the U2.2 gene. The resulting fragment is cut with ClaI and EcoRI and 5' protruding ends are filled in and blunt-ended using Klenow polymerase. The fragment and the vector pDEDH-SP6 from Example E0, linearized with SmaI and dephosphylated, are then ligated to each other. The title plasmid CaMVp/U2/pA, which contains one copy of each of the two fragments, is obtained.

F4) Preparation of the plasmid CaMVp/U2/3'MUT/pA

The preparation is carried out in analogy with Example F3 but using a modified 3' oligonucleotide (45 mer, 5'-GGATCCGAAT TCAAAAGGGG ACGGTCTAGT TCCGCGGGTT GAGCC-3'; SEQ ID NO: 5). This results in the CA dinucleotide at the beginning of the 3' box of the amplified fragment being replaced by the dinucleotide GG and the sequence AGTGAAA at the end of this 3' box being replaced by the sequence CCGTCCC. The title plasmid CaMVp/U2/3'MUT/pA is obtained.

F5) Preparation of the plasmid U2p/13ext/pA

The Arabidopsis U2.2 promoter element is amplified from the plasmid pGEM2.U2.2 (Vankan and Filipowicz, 1989) using a 5' oligonucleotide (23 mer, 5'-ATGAATTCAC TAGTCCCACA TCG-3'; SEQ ID NO: 13), complementary to the sequence of the USE element, and a 3' oligonucleotide (48 mer, 5'-AATCTAGAGG ATCCCCGGGT ACCCTGT-GAA TTGAACGAAT GGCTCAGC-3'; SEQ ID NO: 8), complementary to the U2.2 promoter sequence. The 3' oligonucleotide contains, at the 5' end, an additional 13 base pairs which are complementary to the polylinker region of the plasmid from Example F4. The PCR fragment is cut with EcoRI and KpnI and ligated between the EcoRI and KpnI cleavage sites of the plasmid obtained from Example F4. This results in the CaMV promoter element being replaced by a U2.2 promoter element extended by 13 bp. The title plasmid U2p/13ext/pA is obtained.

F6) Gene expression using the plasmids from Examples F1 to F5

The expression of the plasmids according to the invention is once again investigated using RNAse A/T1 mapping.

Virtually none of the snRNA expressed by the plasmid U2/pA, which possesses an intact 3' box, is polyadenylated. By contrast, considerable quantities of polyadenylated RNA are found in the case of expression from plasmid U2/3'MUT/pA which does not contain an intact 3' box.

Expression from plasmid U2p/13ext/pA, which contains an intact 3' box, also produces snRNA which is not polyadenylated. While plasmid CaMVp/U2/pA also contains an intact 3' box, it expresses a significant proportion of polyadenylated RNA in addition to regular snRNA. On the other hand, plasmid CaMVp/U2/3'MUT/pA contains a mutated 3' box and in the main expresses polyadenylated RNA.

It is clear from the results that the use of an snRNA promoter permits expression of polyadenylated mRNA.

G) Expression of Chimeric Genes using an mRNA Promoter

G1) Preparation of the plasmid GLB/U2/pA

The plasmid prGLB (Hart et al., 1993) is cut with SalI and BamHI, the resulting 5' protruding ends are filled in and blunt-ended using Klenow polymerase, and the 1680 bp-sized fragment, containing the GLB (α-1,3-glucanase) promoter, is isolated. This fragment is ligated between the EcoRI and KpnI cleavage sites of the plasmid obtained from Example F4 once the protruding ends have in this case, too, been blunt-ended with T4 DNA polymerase. The title plasmid GLB/U2/pA, which contains the GLB promoter in place of the CaMV promoter, is obtained.

G2) Preparation of the plasmid GLBΔ60/U2/pA

The plasmid pSP1 (Hart et al., 1993) is cut with XbaI and BamHI, the resulting 5' protruding ends are filled in and blunt-ended using Klenow polymerase, and the 84 bp-sized fragment, containing 60 bp of the GLB promoter, is isolated. This fragment is ligated between the EcoRI and KpnI cleavage sites of the plasmid obtained from Example F4 once the protruding ends have in this case, too, been blunt-ended with T4 DNA polymerase. The title plasmid GLBΔ60/U2/pA, which contains the inactive GLBΔ60 promoter in place of the CaMV promoter, is obtained.

G3) Gene expression using the plasmids from Examples G1 and G2

Expression of the plasmids from Examples G1 and G2 in plant protoplasts is investigated using RNAse A/T1 mapping. In this case, expression of plasmid GLB/U2/pA, which contains an intact 3' box, principally results in non-polyadenylated snRNA and in a relatively small proportion of polyadenylated RNA. On the other hand, expression of plasmid GLBΔ60/U2/pA, which no longer contains any active mRNA promoter, no longer produces any RNA. This signifies, unambiguously, that transcription of non-polyadenylated snRNA from plasmid GLB/U2/pA is initiated by the mRNA promoter of the GLB gene.

H) Transient Expression of Luciferase Driven by Maize U2-27 and Maize U5.1 snRNA Promoters in Maize Callus Tissue H1) Construction of plasmid pVZ1

Plasmid pVZ1 as provided by S. Henikoff is a slightly modified version of the pBS+/− vector from Stratagene (La Jolla, Calif.). In particular, the oligonucleotides OL1 (5'-AATTCGCGGC CGCGGCGCCA ATGCATTGGG CCC-3'; SEQ ID NO: 14) and OL2 (5'-AATTGGGCCC AATG-CATTGG CGCCGCGGCC GCG-3'; SEQ ID NO: 15) are hybridized, kinased and cloned into EcoRI-digested pBS+/−. The resultant plasmid pVZ1 contains an ApaI restriction site at the end of the polylinker region.

H2) Construction of plasmid pEKU2

In a first step the 560 bp XhoI/XbaI fragment containing the maize U2-27 gene (Brown, J. W. S., and R. Waugh, Nucleic Acids Research 17:8991–9001, 1989) is ligated to SalI/XbaI cut pUC18. The resultant plasmid is cut with HindIII and Sau3A and the 227 bp fragment containing the U2-27 promoter element is isolated. The isolated fragment is ligated HindIII/BamHI-digested pVZ1. Ligation results in the title plasmid pEKU2.

H3) Construction of plasmid pEKU2A

Plasmid pEKU2 is cut with HindIII and KpnI and the isolated maize U2 snRNA promoter fragment is ligated into the luciferase reporter plasmid pJD353 (Luehrsen et al, Methods in Enzymology Vol. 216, 397–414, 1992) also cut with HindIII and KpnI. This results in the tide plasmid pEKU2A.

H4) Construction of plasmid pEKU2B

Plasmid pEKU2 is cut with HindIII and KpnI and the isolated maize U2 snRNA promoter fragment is ligated into the luciferase reporter plasmid pJD300 (Luehrsen et al, Methods in Enzymology Vol. 216, 397–414, 1992) also cut with HindIII and KpnI. This results in the title plasmid pEKU2B.

H5) Construction of plasmid pEKU5

A 380 bp BamHI/PvuII fragment containing the maize U5.1 snRNA promoter (Leader et al, Plant Molecular Biology 21:133–143, 1993) is ligated into BamHI/EcoRV-digested pBluescriptKS+(Strategene, La Jolla, Calif.). Ligation results in the title plasmid pEKU5.

H6) Construction of plasmid pEKU5A

Plasmid pEKU5 is cut with BamHI and KpnI and the isolated maize U5.1 snRNA promoter fragment is ligated into the luciferase reporter plasmid pJD353 (Luehrsen et al, Methods in Enzymology Vol. 216, 397–414, 1992) also cut with BamHI and KpnI. This results in the title plasmid pEKU5A.

H7) Construction of plasmid pEKU5B

Plasmid pEKU5 is cut with BamHI and KpnI and the isolated maize U5.1 snRNA promoter fragment is ligated into the luciferase reporter plasmid pJD300 (Luehrsen et al, Methods in Enzymology Vol. 216, 397–414, 1992) also cut with BamHI and KpnI. This cloning step generates the title plasmid pEKU5B.

H8) Transient expression in maize callus tissue

Transient expression of pEKU2A, pEKU2B, pEKU5A, and pEKU5B can be determined as described in Luehrsen et al, Methods in Enzymology Vol. 216, 397–414, 1992. As a control plasmid pEKU5B having the HindIII promoter fragment deleted can be used.

REFERENCE LIST

Birk, Y. et al. 1963. Biochim Biophys Acta 67:326–328.
Bohlmann, A. et al. 1988. EMBO Journal 7:1559–1565.
Brannan et al. 1990. Molecular and Cellular Biology 10:28–36
Brockdorff et al. 1992. Cell 71:515–526
Brown et al. 1992. Cell 71:527–542
Brown, J. W. S., and R. Waugh. 1989. Maize U2 snRNAs: gene sequence and expression. Nucl. Acids Res. 17:8991–9001.
Butler, J. S., and T. Platt. 1988. RNA processing generates the mature 3' end of yeast CYCI mRNA in vitro. Science 242:1270–1274.
Dahlberg, J. E., and E. Lund. 1988. The genes and transcription of the major small nuclear RNAs, p. 38–70. In Birnstiel, M. L. (ed.). Structure and Function of Major and Minor Small Nuclear Ribonucleoprotein Particles. Springer-Verlag, Berlin.
Dahlberg, J. E., and E. T. Schenborn. 1988. The human U1 snRNA promoter and enhancer do not direct synthesis of messenger RNA. Nucl. Acids Res. 16:5827–5840.
Goodall, G. J., and W. Filipowicz. 1989. The AU-rich sequences present in the introns of plant nuclear pre-mRNAs are required for splicing. Cell 58:473–483.
Goodall, G. J., K. Wiebauer and W. Filipowicz. 1990. Methods in Enzymology, Volume 181:148–160.
Goodall, G. J., T. Kiss, and W. Filipowicz. 1991. Nuclear RNA splicing and small nuclear RNAs and their genes in higher plants. Oxford Surveys of Plant Molecular and Cell Biology 7:255–296.
Hart, C. M., F. Nagy, and F. Meins. 1993. A 61 bp enhancer element of the tobacco β-1,3-glucanase B gene interacts with one or more regulated nuclear proteins. Plant Molecular Biology 21:121–131.
Hernandez, N. 1985. Formation of the 3' end of U1 snRNA is directed by a conserved sequence located downstream of the coding region. EMBO J. 4:1827–1837.
Hernandez, N. 1992. Transcription of vertebrate snRNA genes and related genes, p. XXX—XXX. In (S. L. McKnight and K. R. Yamamoto (eds), Transcriptional regulation. Cold Spring Harbor Laboratory Press, Cold Spring Harbor, N.Y.
Hernandez, N., and R. Lucito. 1988. Elements required for transcription initiation of the human U2 snRNA gene coincide with elements required for snRNA 3' end formation. EMBO J. 7:3125–3134.
Hernandez, N., and A. M Weiner. 1986. Formation of the 3' end of U1 snRNA requires compatible snRNA promoter elements. Cell 47:249–258.
Hilder, V. A. et al. 1987. Nature 330:160–163.
Horn et al. 1988. Plant Cell Reports 7:469–472.
Howard et al. 1987. Planta 170:535
Leader et al. Plant Molecular Biology 21:133–143, 1993
Luehrsen et al. Methods in Enzymology Vol. 216, 397–414, 1992
Marshallsay: "Structure, Expression and Evolution of Plant U3 snRNA Genes", Doctoral thesis at the Philosophisch-Naturwissenschaftlichen Facultät (Faculty of Philosophy and Natural Sciences) of the University of Basle, Switzerland
Matsuoka, K. and K. Nakamura. 1991. Proc. Natl. Acad. Sci. USA 88:834–837.
Mogen, B. D., M. H. MacDonald, G. Leggewie, and A. G. Hunt. 1992. Several distinct types of sequence elements are required for efficient mRNA 3' end formation in pea rbcS gene. Mol. Cell. Biol. 12:5406–5414.
Morelli et al. 1985. Nature 315:200–204
Negrutiu, L. et al. 1987. Plant Molecular Biology 8:363–373
Neuhaus et al. 1987. Theoretical and Applied Genetics 74:30–36.

Neuman de Vegvar, H. E., E. Lund, and J. E. Dahlberg. 1986. 3' end formation of U1 snRNA precursors is coupled to transcription from snRNA promoters. Cell 47:259–266.

Parker, R., T. Simmons, E. O. Shuster, P. G. Siliciano, and C. Guthrie. 1988. Genetic analysis of small nuclear RNAs in Saccharomyces cerevisiae: viable sextuple mutant. Mol. Cell. Biol. 8:3150–3159.

Patterson, B., and C. Guthrie. 1987. An essential yeast snRNA with a U5-like domain is required for splicing in vivo. Cell 49:613–624.

Potrykus, I. and R. D. Shillito. 1986. Methods in Enzymology, Volume 118, Plant Molecular Biology, eds. A. and H. Weissbach, Academic Press, Orlando.

Rhodes et al. 1988. Biotechnology 6:56–60.

Sambrook, J., E. F. Fritsch, and T. Maniatis. 1989. Molecular cloning: a laboratory manual. Cold Spring Harbor Laboratory Press, Cold Spring Harbor, N.Y.

Saiki, R. K., D. H. Gelfand, S. Stoffel, S. J. Scharf, R. Higuchi, G. T. Horn, K. B. Mullis, and H. A. Erlich. 1988. Primer-Directed Enzymatic Amplification of DNA with a Thermostable DNA Polymerase. Science 239:487–491.

Sanfaon, H., P. Brodmann, and T. Hohn. 1991. A dissection of the cauliflower mosaic virus polyadenylation signal. Genes Dev. 5:141–149.

Schocher, R. J. et al. 1986. Bio/Technology 4: 1093–1096.

Selsted, M. E. and S. S. L. Harwig. 1987. Infection and Immunity 55:2281–2286.

Shillito, R. D. et al. 1985. Biotechnology 3:1099–1103.

Shillito, R. D. et al. 1989. Biotechnology 7:581–587.

Spena et al. 1985. EMBO Journal 4:2736

Terry, A. S. et al. 1988. Journal of Biological Chemistry 263:5745–5751.

Vankan, P., D. Edoh, and W. Filipowicz. 1988. Structure and expression of the U5 snRNA gene of Arabidopsis thaliana. Conserved upstream sequence elements in plant U-RNA genes. Nucl. Acids Res. 16:10425–10439.

Vankan, P., and W. Filipowicz. 1989. A U-snRNA gene-specific upstream element and a -30 'TATA box' are required for transcription of the U2 snRNA gene of Arabidopsis thaliana. EMBO J. 8:3875–3882.

Wahle, E., and W. Keller. 1992. The biochemistry of 3' end cleavage and polyadenylation of messenger RNA precursors. Ann. Rev. Biochem. 61:419–440.

Wang, Y.-C. 1988. Plant Molecular Biology 11:433–439

Yamada, Y. et al. 1986. Plant Cell Rep 5:85–88.

Yu, K., and R. T. Elder. 1989. Some of the signals for 3' end formation in the transcription of Saccharomyces cerevisiae Ty-D15 element are immediately downstream of the initiation site. Mol. Cell. Biol. 9:2431–2444.

Yuo, C.-Y., M. Ares, Jr., and A.M. Weiner. 1985. Sequences required for 3' end formation of human U2 small nuclear RNA. Cell 42: 193–202.

Zaret, K. S., and F. Sherman. 1984. Mutationally altered 3' ends of yeast CYCL mRNA affect transcription stability and translational efficiency. J. Mol. Biol. 177:107–135.

Patent documentation:

| | | |
|---|---|---|
| U.S. Pat. No. 4,810,777 | EP 186,379 | WO 86/04356 |
| U.S. Pat. No. 4,865,981 | EP 213,318 | WO 88/05826 |
| U.S. Pat. No. 4,996,155 | EP-A 332 104 | WO 89/04371 |
| | EP-A 434,616 | WO 89/07605 |
| | EP-A 459,643 | WO 89/11291 |
| | EP-A 462,065 | |
| | EP-A 478,502 | |

What is claimed is:

1. A chimeric gene construction comprising one promoter element and a 3' termination signal in functional combination with a gene, wherein a) the promoter is an snRNA promoter element from plants specific for RNA polymerase II, b) the 3' termination signal is selected from a group of termination signals which are capable, independently of the promoter element, of signaling the formation of RNA 3' ends, c) the gene codes
   for a polypeptide,
   for sense RNA, for anti-sense RNA or for snRNA, with the proviso that, in the case of the snRNA, the 3' termination signal used in b) represents a eukaryotic Poly(A) signal.

2. A chimeric gene construction according to claim 1, wherein the plant snRNA promoter element encompasses a regulatory DNA element of the formula Ia or Ib in one or more copies (Np)$_n$RpGpCpCpCpR(pN)$_m$ (Ia)

(Np)$_n$YpGpGpGpCpY(pN)$_m$ (Ib)

in which C is cytidine, G is guanosine, R is adenosine or guanosine, Y is cytidine or uridine, N is adenosine, guanosine, cytidine or uridine, p is a phosphate bridge between the 5'-OH group and the 3'-OH group of two nucleosides and n and m are a number between 0 and 10, as well as a functionally equivalent DNA element derived therefrom.

3. A chimeric gene construction according to claim 2, wherein the plant snRNA promoter element is the maize U2-27 or the maize U5. 1 promoter.

4. An expression method comprising transfecting the chimeric gene construction comprising the regulatory DNA element of formula Ia or Ib according to claim 2 into a cell; and obtaining expression of the gene.

5. The expression method of claim 4 wherein the expressed gene is a mRNA gene.

6. A chimeric gene construction according to claim 1, wherein the gene is selected from a group of genes which encode marker genes which are selectable or detectable in plants.

7. A chimeric gene construction according to claim 6, wherein the gene is selected from the group of genes which mediate resistance against kanamycin, G418, methotrexate, hygromycin, bleomycin, aminoethylcysteine, glyophosphate, streptomycin, sulfonylurea, phosphinotricin and gentamycin.

8. A chimeric gene construction according to claim 6, wherein the Arabidopsis U2.2 promoter element, the structural gene of a marker which is selectable in plants, and the CaMV poly(A) signal are used.

9. A chimeric gene construction according to claim 6, wherein the gene is selected from the group comprising β-glucoronidase, choloramphenicol acetyl transferase and luciferase.

10. A chimeric gene construction according to claim 1, wherein the gene is selected from a group of genes which encodes proteins which protect plants against pathogens, herbicides, fungicides, insecticides, or disadvantageous environmental influences, wherein the disadvantageous environmental influences comprise heat, cold, wind, unfavorable soil conditions, moisture and dryness.

11. A chimeric gene construction according to claim 10, wherein the gene is selected from a group of genes which code for a crystalline protein form *Bacillus thuringensis*, chitinase, β-1,3,-glucanase, EPSP synthase, acetolactate synthase, glutamine synthase, and Stretomyces PATE.

12. A chimeric gene construction according to claim 10, wherein the Arabidopsis U2.2 promoter element, the gene of a protein which protects plants against pathogens, herbicides, fungicides insecticides or disadvantageous environmental influences, wherein the disadvantageous environmental influences comprise heat, cold, wind, unfavorable soil conditions, moisture and dryness, and the CaMV Poly {A} signal are used.

13. A chimeric gene construction according to claim 1, wherein the gene represents a synthetic gene which encodes a peptide, sense RNA or anti-sense RNA.

14. A chimeric gene construction according to claim 13, wherein the Arabidopsis U2.2 promoter element, a structural gene which encodes a peptide, and the CaMV poly(A) signal are used.

15. A method of transfection comprising transfecting the chimeric gene construction according to claim 1 into a plant cell.

16. An expression method comprising expressing the chimeric gene construction according to claim 1, in a plant cell.

17. A chimeric gene construction comprising a promoter element and a 3' termination signal in functional combination with a gene, wherein a) the promoter is an mRNA promoter element from a plant, b) the 3' termination signal contains a plant snRNA 3', and c) the gene codes for snRNA, tRNA, rRNA, sense RNA or anti-sense RNA.

18. An expression method comprising transfecting the chimeric gene construction according to claim 1 or 2 into a plant cell wherein the gene is a synthetic gene; and expressing the synthetic gene.

19. A chimeric gene construction according to claim 17, wherein the mRNA promoter element is the 35S or 19S Cauliflower Mosaic Virus promoter, the β-1,3-glucanase promoter, the nopaline synthase promoter or the octopine synthase promoter.

20. A chimeric gene construction according to claim 17, wherein a Cauliflower Mosaic Virus promoter element, a synthetic structural gene coding for sense RNA or anti-sense RNA, and the Arabidopsis U2.2 3' box are used.

21. A plasmid having the ability to replicate in a microorganism, which plasmid contains, integrated in its DNA sequence, a chimeric gene construction according to any one of claims 1–3 6–8, 10–14, 17, 19 or 20.

22. A process for preparing plasmids according to claim 21 wherein a) the individual elements of the chimeric gene construction are covalently bonded to each other in the desired plasmid vector using recombinant DNA methods, b) the resulting plasmid is transformed into a microorganism using transformation methods, and c) the plasmid is subsequently isolated from the transformed microorganism, and purified applying methods of lysis and purification.

23. A preparation process according to claim 22, wherein *E. coli*, Bacillus, Agrobacterium or yeast is used for the transformation step b).

24. A microorganism which contains and replicates a plasmid according to claim 21.

25. A method of transfection comprising transfecting a chimeric gene construction according to claim 21 into a plant cell.

26. An expression method comprising transfecting a plasmid according to claim 21 into a plant cell; and expressing the synthetic gene.

27. A plasmid having the ability to replicate in *E. coli*, Bacillus, Agrobacterium or yeast, which plasmid contains, integrated in its DNA sequence, a chimeric gene construction according to any one of claims 1–3 6–8, 10–14, 17, 19 or 20.

28. A microorganism which contains and replicates a plasmid according to claim 27.

29. A method of transfection comprising transfecting a chimeric gene construction according to claim 27 into a plant cell.

30. An expression method comprising transfecting a plasmid according to claim 27 into a plant cell; and obtaining expression of the gene.

31. A shuttle vector having the ability to replicate in Agrobacterium and a microorganism selected from the group *E. coli*, Bacillus and yeast, which vector contains, integrated in its DNA sequence, a chimeric gene construction according to any one of claims 1–3 6–8 10–14, 17, 19 or 20.

32. A process for preparing plasmids according to claim 31 wherein
   a) the individual elements of the chimeric gene construction are covalently bonded to each other in the desired plasmid vector using recombinant DNA methods,
   b) the resulting plasmid is transformed into a microorganism using transformation methods, and
   c) the plasmid is subsequently isolated from the transformed microorganism, and purified applying methods of lysis and purification.

33. A microorganism which contains and replicates a plasmid according to claim 31.

34. A method of transfection comprising transfecting a chimeric gene construction according to claim 31 into a plant cell.

35. An expression method comprising transfecting a plasmid according to claim 31 into a plant cell; and obtaining expression of the gene.

36. A binary Ti or Ri vector, which contains, integrated in its DNA sequence, a chimeric gene construction according to any one of claims 1–3 6–8, 10–14, 17, 19 or 20.

37. A process for preparing plasmids according to claim 36 wherein
   d) the individual elements of the chimeric gene construction are covalently bonded to each other in the desired plasmid vector using recombinant DNA methods,
   e) the resulting plasmid is transformed into a microorganism using transformation methods, and
   f) the plasmid is subsequently isolated from the transformed microorganism, and purified applying methods of lysis and purification.

38. A microorganism which contains and replicates a plasmid according to claim 36.

39. A method of transfection comprising transfecting a chimeric gene construction according to claim 36 into a plant cell.

40. An expression method comprising transfecting a plasmid according to claim 36 into a plant cell; and obtaining expression of the gene.

41. A process for preparing a chimes gene construction according to any one of claims 1–3, 6–8, 10–14, 17, 19 or 20, wherein methods of organochemical polynucleotide synthesis are used either on their own or in combination with recombinant DNA methods.

42. A plant cell, which expresses a chimeric gene construction according to any one of claims 1–3 6–8 10–14, 17, 19 or 20.

43. An entire fertile plant, which expresses a chimeric gene construction according to any one of claims 1–3, 6–8, 10–14 17, 19 or 20.

44. A plant material which can be regenerated to form an entire fertile plant, which material expresses a chimeric gene construction according to any one of claims 1–3, 6–8, 10–14, 17, 19 or 20.

45. Asexual and/or sexual descendants of a transgenic plant, which descendants express a chimeric gene construction according to any one of claims 1–3, 6–8, 10–14 17, 19, or 20.

* * * * *